United States Patent [19]

Chmelir et al.

[11] Patent Number: 4,693,713

[45] Date of Patent: Sep. 15, 1987

[54] ABSORBENTS FOR BLOOD AND SEROUS BODY FLUIDS

[76] Inventors: Miroslav Chmelir, Grönkesdyk 36, 4150 Krefeld; Kurt Dahmen, von-Velsen.str.6, Möchengladbach; Georg Hoffman, Westwall 165, 4150 Krefeld; Georg Werner, Dresdner Str.7, 4154 Tönisvorst 1, all of Fed. Rep. of Germany

[21] Appl. No.: 928,573

[22] PCT Filed: Jul. 10, 1982

[86] PCT No.: PCT/DE82/00146

§ 371 Date: Mar. 10, 1983

§ 102(e) Date: Mar. 10, 1983

[87] PCT Pub. No.: WO83/00289

PCT Pub. Date: Feb. 3, 1983

Related U.S. Application Data

[63] Continuation of Ser. No. 485,128, Jun. 15, 1983, abandoned.

[30] Foreign Application Priority Data

Jul. 16, 1981 [DE] Fed. Rep. of Germany ....... 3128100

[51] Int. Cl.⁴ ............................................. A61F 13/16
[52] U.S. Cl. .................................... 604/368; 604/358; 128/156
[58] Field of Search ................ 604/368, 360; 128/155, 128/156

[56] References Cited

U.S. PATENT DOCUMENTS

| | | | |
|---|---|---|---|
| 3,121,427 | 2/1964 | Mosier | 604/368 |
| 3,810,468 | 5/1974 | Harper et al. | 604/368 |
| 4,058,124 | 11/1977 | Yen et al. | 604/368 |
| 4,076,663 | 2/1978 | Masuda et al. | 604/368 |
| 4,190,563 | 2/1980 | Bosley et al. | 604/368 |
| 4,259,383 | 3/1981 | Eggensperger et al. | 604/360 |
| 4,333,461 | 6/1982 | Muller | 604/368 |

Primary Examiner—C. Fred Rosenbaum
Assistant Examiner—Sherri E. Vinyard
Attorney, Agent, or Firm—Brumbaugh, Graves, Donohue & Raymond

[57] ABSTRACT

The invention concerns an absorbent for blood and serous body fluids consisting of at least two components, A and B, whereby component A is a crosslinked synthetic or natural polymer or copolymer, and component B is an organic and/or inorganic compound which is water-soluble and solid at normal temperature. The absorbent contains 25 to 98 weight % of component A and 2 to 75 weight % of component B. The invention, moveover, concerns the use of the said absorbent for absorption and/or retention of blood and serous body fluids, in particular in absorbent throwaway articles for surgical, medical and hygienic purposes.

19 Claims, No Drawings

ABSORBENTS FOR BLOOD AND SEROUS BODY FLUIDS

This application is a continuation of application Ser. No. 485,128, filed on 6/15/83, now abandoned.

The invention concerns absorbents for blood and other serous body fluids which are suitable for use in absorbent throw-away products for surgical and other medical purposes as well as for sanitary napkins.

In recent years was developed a number of different polymerizates which had high absorption capacity for water and body fluids. Most of these products were based on starch, such as, e.g., starch-acrylonitrile graft polymerizates (U.S. Pat. Nos. 3,997,484; 3,661,815; 4,155,888; 3,935,099), gelatinized starch derivatives (DE-OS No. 2,702,781), starch-acryloamide-acryloamidopropane sulphonic acid graft polymerizate (U.S. patent application Ser. No. 955,827), or on cellulose, such as derivatives of alkyl or hydroxyalkyl cellulose (Jap. Pat. No. 77/125.481), carboxymethyl cellulose (Belg. Pat. No. 862,130; GBP No. 1,159,949) and on polysaccharides (DE-OS No. 2,650,377). The fully synthetic absorbents described in numerous patents comprise crosslinked acrylic or methacrylic acid polymers and copolymers (DE-OS No. 2,429,236; DE-OS No. 2,614,662; U.S. Pat. Nos. 4,018,951; 3,926,891; 4,066,583; 4,062,817; DE-OS No. 2,712,043; DE-OS No. 2,653,135; DE-OS No. 2,650,377; DE-OS No. 2,813,634) or maleic acid derivatives (U.S. Pat. No. 4,041,228).

All of these products are practically insoluble in water, absorb a multiple of their weight in water, urine or other aqueous solutions but are practically without absorption capacity for blood because of their low dispersibility in blood.

On first contact with blood of the polymer absorbents constituting the state of the art, a skin forms on the drop of blood which acts as barrier against the penetration of the blood towards the absorbent particles. There result non-wetted absorbent particles and a drop of blood with a solid skin which on the inside, however, is filled with liquid blood.

A partial improvement of blood dispersibility of the absorbent was obtained in accordance with DE-OS No. 2,844,956 and EUP No. 0,009,977 in that a partly synthetic or fully synthetic absorbent in powder form is subsequently treated with polyethers (DE-OS No. 2,844,956) or with fat alcohols, fatty acids or fat esters (EUP No. 0,009,977), mostly dissolved in organic solvents.

Surprisingly, it was found that addition to the polymer absorbent of an inorganic or organic water-soluble compound present at normal temperature in form of a pourable powder is capable of accelerating the capillar flow of the blood through the mass of the particulate absorbent. In this manner, rapid distribution of the blood within the entire absorbent mass is achieved so that the blood can be absorbed at a faster rate.

The subject of the invention is an absorbent for blood and serous body fluids which is characterized in that it comprises at least two components, A and B, whereby component A is at least one water-swellable synthetic or natural polymer or copolymer and component B is at least one inorganic and/or organic compound which at normal temperature is present in form of a pourable powder and is water-soluble.

Suitable as Component A are the water-swellable polysaccharide polymers, such as cellulose, cellulose derivatives, such as carboxymethyl cellulose, alkyl or hydroxyalkyl cellulose, starch and starch derivatives and natural gums (xanthan gum, alginic acid) and their salts as well as the polymers and copolymers of (meth)acrylic acid or (meth)acrylic acid derivatives, mainly homo- or copolymers of acrylic, methacrylic, acrylamidomethylpropane sulphonic acid, the salts of the aforegoing acids; of acrylic or methacrylic amide with each other or with vinyl pyrrolidone and/or vinyl acetate. The aforementioned polymers may be crosslinked by at least one bifunctional netting agent so that they are only swellable but not soluble in water. All of the polymers are produced in accordance with known methods.

Suitable as component B are inorganic or organic compounds which are solid at ambient temperature, preferably in form of a pourable powder.

Especially suitable as Component B are water-soluble salts of organic or inorganic acids not injurious to health, inorganic acids or organic mono- or polycarboxylic acids or low-molecular polymer carboxylic or sulphonic acids, solid at normal temperature, powdered and not injurious to health or also derivatives of carboxylic acids or mono- and oligosaccharides solid at normal temperature and not injurious to health.

As salts of inorganic acids which are not injurious to health are preferred the chlorides, bromides, iodides, sulphates, hydrosulphates, phosphates, hydrogen or dihydrogen phosphates, tetraborates, nitrates, carbonates or hydrogen carbonates, as salts of organic carboxylic acids the salts of acetic, formic, adipic, citric or tartaric acids or also the salts of low-molecular polymeric carboxylic and/or sulphonic acids having molecular masses ranging from 300 to 100,000, preferably 2,000 to 20,000, of homo- or copolymerizates of unsaturated mono- or dicarboxylic acids, sulphonic acids, aldehydes, alcohols as well as (meth)acryloamide.

Suitable salts are the ammonium, sodium, potassium, lithium, calcium, magnesium, zinc, aluminum or iron salts of the inorganic or organic acid.

There may also be used inorganic or organic acids proper as component B, provided they are solid at normal temperature, are powdered and water-soluble. Suitable inorganic acids are boric acid or phosphoric acid. Suitable organic acids are mono- or polycarboxylic acids, such as citric, tartaric or adipic acid or low-molecular polymeric carboxylic or sulphonic acids with molecular masses ranging from 300 to 100,000 g/mole, preferably 2,000 to 20,000 g/mole based on homo- or copolymerizates of unsaturated mono- or dicarboxylic acids, sulphonic acids, aldehydes, alcohols as well as (meth)acrylamide.

Suitable are, furthermore, the water-soluble derivatives of carboxylic acid, solid at normal temperature, such as amides or diamides, preferably acetamide, urea and urea derivatives, such as thiourea, methyl or ethyl urea.

Finally, there are also suitable as component B mono- or oligosaccharides, such as glucose, fructose, mannose or saccharose.

The absorbent is composed of components A and B at a weight ratio of 25 to 98 weight %, preferably 50 to 90 weight %, of component A to 2 to 75 weight %, preferably 10 to 50 weight %, of component B.

Mixing of the two components, A and B, may be obtained in that component B is already dissolved in the monomer solution prior to polymerization, or in that component B is added to the process at any time in dry or dissolved form.

The absorbent in accordance with the invention, due to its composition, is suitable to absorb and/or retain blood and other serous body fluids, in particular for use in absorbent throw-away products, such as sanitary napkins, tampons or absorbent products for surgical and medical purposes.

Depending on the intended use, the absorbent in accordance with the invention is sprinkled onto or over a textile or paper support in some suitable dosage and is fixed in or on the material by some suitable measures.

The absorbents in accordance with the invention may be mixed with perfumes, binders or other adjuvants, too, such as, e.g., disinfectants, which do not influence the absorption properties of the absorbent.

The production of component A is explained in Examples 1 to 6.

EXAMPLE 1

In a polymerization vessel were dissolved in 980 g water 328 g acrylic acid, 2.6 g N,N'-methylene bisacryloamide and were adjusted to pH=4.0 by means of 127.5 g sodium hydrogen carbonate. The components of the catalyst system (0.36 g azobisamidine propane dihydrochloride, 0.73 g potassium persulfate, 1.34 g sodiumpyrosulfite and 0.06 g iron(II)gluconate) dissolved in 120 ml water were added at normal temperature whereby adiabatic polymerization was achieved. The polymer gel obtained was divided, dried and ground.

EXAMPLE 2

In a polymerization vessel were dissolved 375 g acrylic acid and 0.75 g N,N'methylene bisacryloamide in 850 g water and neutralized to a pH=4.0 by means of 120 g of a 25% ammonia solution. The same catalyst system as in Example 1 was employed for polymerization and the polymer gel obtained was treated in the same manner.

EXAMPLE 3

In a polymerization vessel 140 g acryloamide, 35.6 g acrylic acid and 1.8 g N,N'-methylene bisacryloamide were dissolved in 550 g distilled water and neutralized to pH=4.0 by means of 10 g sodium hydrogen carbonate. The individual components of the catalyst system (0.64 g sodium pyrosulfate, 0.36 g potassium persulfate and 0.03 g iron(II) gluconate dissolved in 60 g water were added at normal temperature whereby polymerization was started. Processing occurred as in Example 1.

EXAMPLE 4

In a polymerization vessel 568 g acrylic acid, 0.75 g tetraallyl oxyethane and 181.5 g acryloamide propanesulfonic acid were dissolved in 1930 g water and neutralized to a pH=4.5 with 256 g sodium hydrogen carbonate. Following addition of 1.2 g azobisamidine propanedihydrochloride photochemical polymerization is obtained at normal temperature by UV light. The polymer gel was reduced, dried and ground.

EXAMPLE 5

In a polymerization vessel 328 g methacrylic acid, 48 g vinyl pyrrolidone and 0.75 g trimethylol propanediallyl ether were dissolved in 100 g water and neutralized with 34.6 sodium hydrogen carbonate to a pH=4.2. 0.6 g azobisamidine propane dihydrochloride was added and photochemical polymerization was effected. The polymer gel was processed as in Example 1.

EXAMPLE 6

In a polymerization vessel 320 g acrylic acid, 56 g vinyl pyrrolidone and 3.75 g N,N'-methylene bisacryloamide were dissolved in 862 g water and neutralized to a pH=4.4 by means of 100 g sodium hydrogen carbonate. The individual components of the catalyst system (0.6 g azobisamidine propane dihydroxychloride, 1.2 g sodium pyrosulfite and 0.6 g potassium persulfate) were added dissolved in 150 g water at normal temperature. Polymerization occurred practically adiabatically. The polymer gel obtained was comminuted, dried and ground.

EXAMPLE 7

In a polymerization vessel 320 g acrylic acid, 56 g vinyl pyrrolidine, 3.75 g N,N' methylene bisacryloamide and 54 g sodium chloride were dissolved in 700 g water and neutralized to pH=4.0 with 125 g sodium hydrogen carbonate. 0.6 g azobisamidine propane dihydrochloride was added at normal temperature and polymerization was obtained photochemically (by UV light). The resulting polymer gel was comminuted, dried and ground.

EXAMPLE 8

To the products obtained as per Examples 1 to 6 (component A) were mixed in powder form homogeneous the salts indicated in Table 1 (component B). The following testing method was employed in order to determine the speed of distribution of the blood in the absorbent and the quantity of blood retained by the absorbent:

On a filter paper layer ($\phi$45 mm) was placed a plexiglas plate with a round cutout ($\phi$40 mm). The absorbent to be tested was sprinkled into the opening and distributed uniformly over the entire circular surface. Thereafter, 0.5 ml human blood was placed in the center of the circle and the time in which the blood stain forming due to capillary forces attained a size of 20 mm was measured. After 60 seconds, the test specimen was covered with filter paper ($\phi$45 mm), was weighted down with a 500 g weight (40 g/cm$^2$) and the quantity of blood absorbed due to the absorbent was determined, whereby the quantity of non-used-up absorbent as well as the blood quantity absorbed by the filter paper cover and filter base was taken into account. The results appear in Table 1.

In the same manner were also tested the absorbents in accordance with the invention which were produced from polymerizates on a natural basis (component A). The results appear in Table 2.

TABLE 1

| Component A | Component B | Ratio A/B | Absorbed blood quant. in % relative to used blood quantity | Component A | Speed of blood distribution in sec. |
|---|---|---|---|---|---|
| Example 1 | — | — | 34.0 | — | >60 |
| " | KCl | 2:1 | 74.0 | 68 | 3 |
| " | KCl | 3:1 | 74.6 | 85 | 4 |
| " | KCl | 5:1 | 90.6 | 98 | 11 |
| " | KCl | 7:1 | 85.2 | 100 | 12 |
| " | KCl | 9:1 | 81.8 | 110 | 30 |
| " | KCl | 19:1 | 64.4 | 140 | 48 |
| " | $NH_4Cl$ | 5:1 | 84.6 | 83 | 3 |
| " | NaCl | 5:1 | 83.6 | 78 | 10 |
| " | $Na_2SO_4$ | 5:1 | 77.2 | 100 | 5 |
| " | KBr | 3:1 | 92.0 | 88 | 4 |
| " | $KHSO_4$ | 3:1 | 89.0 | 95 | 7 |
| " | $K_2SO_4$ | 3:1 | 91.0 | 105 | 4.5 |
| " | $KNO_3$ | 2:1 | 89 | 91 | 11 |
| " | $NaNO_3$ | 2:1 | 87 | 89 | 12 |
| " | $NaNH_4HPO_4$ | 3:1 | 88 | 98 | 12 |
| " | $NaPO_3$ | 3:1 | 90 | 96 | 18 |
| " | $NH_4H_2PO_4$ | 3:1 | 86 | 102 | 12 |
| " | o-Phosphoric acid | 3:1 | 95 | 135 | 16 |
| " | m-Phosphoric acid | 3:1 | 81 | 77 | 24 |
| " | boric acid | 3:1 | 45 | 198 | 48 |
| " | $Na_2B_4O_7.10 H_2O$ | 3:1 | 95 | 101 | 48 |
| " | $CaCl_2$ | 3:1 | 79 | 78 | 30 |
| " | $NH_4Fe(SO_4)_2$ | 3:1 | 81 | 85 | 14 |
| " | $Ca(CH_3COO)_2$ | 3:1 | 91 | 110 | 6 |
| " | $Ca(H_2PO_4)_2$ | 3:1 | 90 | 98 | 18 |
| " | $CaCO_3$ | 3:1 | 92 | 85 | 16 |
| " | $K Al(SO_4)_2$ | 5:1 | 87.3 | 138 | 18 |
| " | $Al_2(SO_4)_3$ | 5:1 | 90.1 | 108 | 16 |
| " | $CH_3COOK$ | 5:1 | 82.5 | 194 | 3 |
| " | $CH_3XOONa$ | 4:1 | 90.7 | 125 | 4 |
| " | $CH_3COONa$ | 9:1 | 90.0 | 147 | 5 |
| " | $(CH_3COO)_2Mg$ | 5:1 | 93.0 | 114 | 4 |
| " | potassium tartrate | 3:1 | 85.0 | 102 | 18 |
| " | sodium citrate | 3:1 | 91.0 | 110 | 12 |
| " | $CH_3CONH_2$ | 4:1 | 100.0 | 130 | 5 |
| " | Saccharose | 4:1 | 78.0 | 240 | 55 |
| " | Glucose | 4:1 | 95.9 | 195 | 15 |
| " | Citric acid | 4:1 | 92.6 | 180 | 13.6 |
| " | citric acid/KCL (1:1) | 4:1 | 100.0 | 120 | 8.5 |
| " | urea | 4:1 | 99.0 | 114 | 8.8 |
| " | Ethyl urea | 4:1 | 98.1 | 138 | 12.4 |
| Example 2 | — | — | 40.1 | — | <60 |
| " | KCl | 5:1 | 85.6 | 94 | 4 |
| Example 3 | — | — | 45.0 | — | <60 |
| " | NaCl | 3:1 | 79.0 | 96 | 45 |
| Example 4 | — | — | 53.1 | — | <60 |
| " | KCl | 5:1 | 93.5 | 82 | 3.5 |
| Example 5 | — | — | 55.0 | — | <60 |
| " | NaCl | 2:1 | 95.0 | '81 | 15 |
| Example 6 | — | — | 61.5 | — | <60 |
| " | KCl | 5:1 | 75.3 | 85 | 12 |
| " | NaCl | 1:1 | 85.5 | 90 | 2 |
| " | $NH_4Cl$ | 2:1 | 90.1 | 112 | 15 |
| " | $Na_2HPO_4$ | 2:1 | 88.0 | 102 | 18 |
| " | Na—Polyacrylate Mol. wt 4000 g/mol | 4:1 | 72.0 | 190 | 12 |
| " | Na—Acrylate/ Acrylamide-Co polymerizate Mol. wt. 9000 g/mol | 3:1 | 85.0 | 120 | 17 |
| " | Acrylic acid/ 2-Acrylami-do-2-methyl-propanesulfonic acid-Copoly- | 3:1 | 91.0 | 118 | 12 |

TABLE 1-continued

| Component A | Component B | Ratio A/B | Absorbed blood quant. in % relative to used blood quantity | Absorbed blood quant. in % relative to used Component A | Speed of blood distribution in sec. |
|---|---|---|---|---|---|
| Example 7 | merizate Na—salt Mol. wt. 15000 g/mol. NaCl | 6:1 | 94.5 | 96 | 3 |
| " | NaCl/KCl (1:1) | 7:3 | 95.0 | 83 | 3 |
| Polyacrylamide Mol. wt 5.10$^6$ g/mol | $CH_3COONa$ | 4:1 | 81.0 | 143 | 14.0 |
| Polyacrylamide Mol. wt. 1.10$^6$ g/mol | — | — | 42.7 | 94 | 35.0 |
| Polyacrylamide Mol. wt. 1.10$^6$ g/mol | Ethyl urea | 3:1 | 70.0 | 123 | 14.0 |
| Polyacrylamide Mol. wt. 1.10$^6$ g/mol | $CH_3COONa$ | 3:1 | 58.0 | 84 | 13.2 |
| Acrylamide/ Acrylic acid Copolymerizate Mol. wt. 6.10$^6$ g/mol | $CH_3COONa$ | 4:1 | 75.0 | 134 | 14.4 |

TABLE 2

| Component A | Component B | Ratio A/B | Absorbed blood quant. in % relative to used blood quantity | Absorbed blood quant. in % relative to used Component A | Speed of blood distribution in sec. |
|---|---|---|---|---|---|
| crosslinked starch Arylic acid Copolymerizate | — | — | 15.0 | — | >60 |
| crosslinked starch Arylic acid Copolymerizate | KCl | 2:1 | 37.0 | 180 | 60 |
| crosslinked starch Arylic acid Copolymerizate | KCl | 1:1 | 55.1 | 250 | 45 |
| crosslinked starch Arylic acid Copolymerizate | KCl | 1:3 | 85.5 | 380 | 13.5 |
| Carboxymethylcellulose | — | — | 18.0 | — | <60 |
| Carboxymethylcellulose | $CH_3COONa$ | 1:1 | 94.0 | 180 | 14 |
| Methylhydroxyethylcellulose | — | — | 12 | — | <60 |
| Methylhydroxyethylcellulose | $CH_3COONa$ | 1:1 | 79.2 | 184 | 45 |
| Cellulose MN 100 | — | — | 24.0 | — | <60 |
| Cellulose MN 100 | $CH_3COONa$ | 1:1 | 88.9 | 230 | 17.9 |
| starch | — | — | 18.0 | — | <60 |
| " | $CH_3COONa$ | 1:2 | 87.3 | ~150 | 45 |

We claim:

1. An absorbent for blood or other serious body fluids comprising a physical mixture of components A and B wherein:
   component A is at least one compound selected from the group consisting of water-swellable and water-insoluble synthetic and natural polymers and copolymers; and
   component B is at least one compound not harmful to health which is water soluble and present in the form of a pourable powder at ambient temperature selected from the group consisting of thiourea, methyl urea, ethyl urea, acrylamide, methacrylamide, monosaccharides, oligosaccharides, inorganic acids, monocarboxylic acid, polycarboxylic acid, amides of carboxylic acids, salts of monocarboxylic acids and salts of polycarboxylic acids.

2. An absorbent according to claim 1 wherein component A includes at least one compound selected from the group consisting of polymers and copolymers of acrylic acid or methacrylic acid, and polymers and copolymers of salts and amides of acrylic acid or methacrylic acid.

3. An absorbent according to claim 2 wherein component A includes at least one compound selected from the group consisting of (i) polymers of acrylic acid, methyacrylic acid, acrylamidomethylpropane sulphonic acid, the salts of the said acids, acrylamide and methacrylamide, (ii) copolymers of the foregoing with one another, and (iii) copolymers of the foregoing with vinyl pyrrolidone, vinyl acetone or both.

4. An absorbent according to claim 1 wherein component A includes a cross-linked polysaccharide polymer or copolymer.

5. An absorbent according to claim 4 wherein said component A includes at least one cross-linked compound selected from the group consisting of starch, cellulose and derivatives thereof.

6. An absorbent according to claim 1 wherein said component B includes at least one compound selected from the group consisting of chlorides, bromides, iodides, sulphates, hydrosulphates, phosphates, hydrogen or dihydrogen phosphates, tetraborates, nitrates, carbonates and hydrogen carbonates.

7. An absorbent according to claim 1 wherein component B includes at least one salt of a carboxylic acid selected from the group consisting of acetic, formic, adipic, citric and tartaric acids.

8. An absorbent according to claim 1 wherein component B includes a salt of a polymeric carboxylic or sulphonic acid having a molecular weight ranging between 300 and 100,000, which polymeric acids are derived from homo- and copolymer of unsaturated mono and dicarboxylic acids, sulphonic acids, alcohols and copolymers of said acids with unsaturated aldehydes, or methacrylamide.

9. An absorbent according to claim 8 wherein said polymeric acid has a molecular weight between 2,000 and 20,000.

10. An absorbent according to claims 1 or 5 wherein said component B includes at least one salt selected from the group consisting of ammonium, sodium, potassium, lithium, calcium, magnesium, zinc, aluminum and iron salts not injurious to health of an organic or inorganic acid.

11. An absorbent according to claim 1 wherein said inorganic acid includes phosphoric acid or boric acid.

12. An absorbent according to claim 1 wherein said component B includes at least one compound selected from the group consisting of citric, tartaric and adipic acids.

13. An absorbent according to claim 1 wherein said component B includes a low-molecular weight polymeric carboxylic or sulphonic acid having a molecular weight ranging from 300 to 100,000 grams per mole, and is based on a homo- or copolymer of an unsaturated mono or dicarboxylic acid, or a copolymer of said acids with an unsaturated aldehyde or sulphonic acid, alcohol or methacrylamide.

14. An absorbent according to claim 13 wherein said polymeric acid has a molecular weight between 2,000 and 20,000.

15. An absorbent according to claim 14 wherein said component B includes glucose, fructose, mannose or saccharose.

16. An absorbent according to claim 1 wherein said absorbent contains from 10% to 98% by weight of component A and from 2% to 90% by weight of component B.

17. An absorbent according to claim 16 wherein said absorbent contains from 50% to 90% by weight of component A and from 10% to 59% by weight of component B.

18. An article for use in absorbing blood or other serous fluids comprising a textile or paper support which carries an effective amount of an absorbent according to claim 1.

19. The method for absorbing blood or serous body fluids comprising contacting the blood or serous body fluid to be absorbed with an effective amount of an absorbent according to claim 1.

* * * * *